United States Patent [19]

Garlaschelli et al.

[11] Patent Number: 4,477,461
[45] Date of Patent: Oct. 16, 1984

[54] N-ARYL-N-ACYL-3-AMINO-1,3-OXAZOLIDINE-2-THIONES HAVING FUNGICIDAL ACTIVITY

[75] Inventors: Luigi Garlaschelli, Pavia; Franco Gozzo, S. Donato Milanese; Vincenzo Mendillo, Paullo; Carlo Garavaglia, Cuggiono; Luigi Mirenna, Milan; Angela Zagni, Peschiera Borromeo, all of Italy

[73] Assignee: Montedison S.p.A., Milan, Italy

[21] Appl. No.: 426,893

[22] Filed: Sep. 29, 1982

[30] Foreign Application Priority Data

Oct. 1, 1981 [IT] Italy ................................ 24245 A/81

[51] Int. Cl.[3] ................... C07D 263/26; A01N 43/76

[52] U.S. Cl. .................................... 424/272; 548/230; 564/305; 564/152

[58] Field of Search .................... 548/230; 424/272

[56] References Cited

FOREIGN PATENT DOCUMENTS 2058059 4/1981 United Kingdom ................ 548/230

Primary Examiner—Donald G. Daus
Assistant Examiner—S. A. Gibson

[57] ABSTRACT

Fungicidal compounds belonging to the class of N-aryl-N-acyl-3-amino-1,3-oxazolidine-2-thiones and the processes for synthesizing them are herein described.

The utilization of such compounds to control infections due to phytopathogenous fungi is described too.

7 Claims, No Drawings

N-ARYL-N-ACYL-3-AMINO-1,3-OXAZOLIDINE-2-THIONES HAVING FUNGICIDAL ACTIVITY

BACKGROUND OF THE INVENTION

Belgian Pat. No. 885,117 (Montedison S.p.A.) describes N-aryl-N-acyl-3-amino-1,3-oxazolidine-2-ones endowed with fungicidal activity. Although these compounds possess many positive characteristics such as, for example, a high fungicidal activity combined with a good compatibility with the superior plants, they exhibit also a few properties which could condition a correct and ecologically harmless application in the agrarian field such as, for instance, a high hydrophily and a high persistence.

By consequence, the finding of new compounds, which possess besides the favourable biological properties also different chemical-physical characteristics capable of leading to an overcoming of any problems which may arise with the compounds of the known classes, represents a progress.

THE PRESENT INVENTION

We have now found compounds having the formula:

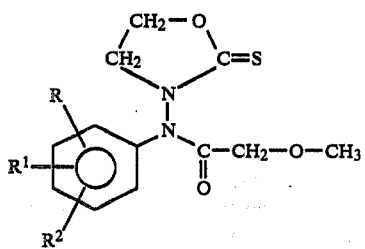

wherein R, R$^1$ and R$^2$, equal to or different from each other, represent a hydrogen atom, a $C_1$-$C_4$ alkyl, a halogen atom, a $C_1$-$C_4$ alkoxyl.

The compounds of formula I are endowed with a high fungicidal activity and a low phytotoxicity and are therefore suited to be employed in the defense of the cultures against infections caused by fungi.

As compared with the compounds described in Belgian Pat. No. 885,117 cited hereinabove, the compounds according to this invention exhibit some more favourable characteristics, such as e.g. a lower hydrophilic degree and a broader activity range.

In addition, the compounds of formula I are endowed with a correct persistence of action, which is sufficient for the practical applications in agriculture, without being excessive.

To prepare the compounds of the present invention, several synthesis processes, described hereinbelow, are possible, the choice of them depending on various factors such as, e.g., the particular compounds to be prepared, the available starting products, economical considerations, and the like.

In the description of the synthesis processes reported hereinafter, symbols R, R$^1$ and R$^2$, have the same meanings specified for formula I, furthermore symbol Ar is used to indicate the aryl radical of formula:

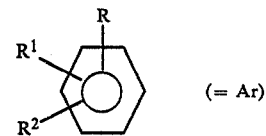

The final step of the process consists in reacting with thiophosgene ($CSCl_2$) a compound of formula

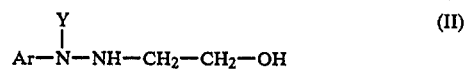

wherein Y is a hydrogen atom (II-A) or an acyl radical of formula

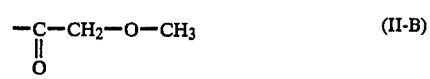

The reaction of intermediate II-B with thiophosgene directly provides the compounds of formula I.

The reaction of intermediate II-A with thiophosgene provides, conversely, another intermediate of formula:

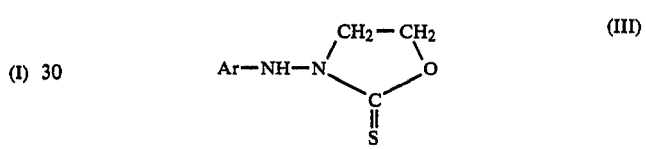

The compounds of formula I are therefore obtained by acylating intermediate III by means of a proper acyl halide of formula:

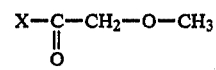

(where X=Cl, Br).

The reaction between intermediates II and thiophosgene is accomplished in an inert solvent and in the presence of a halogenhydric-acid-accepting base in an at least bimolecular amount in respect of thiophosgene.

The preparation of intermediate II-A may be accomplished by alkaline hydrolysis of 3-arylamino-1,3-oxazolidin-2-ones of formula:

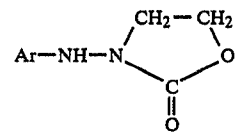

described in Belgian Pat. No. 885,117.

As an alternative, compounds II-A may be prepared according to the reaction shown in following Scheme 1.

SCHEME 1

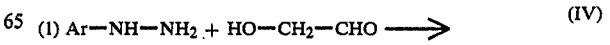

-continued (2) (IV) $\xrightarrow{\text{Reducers}}$ II-A

Reaction 1 of Scheme 1 consists in condensing an aryl-hydrazine with a glycolic aldehyde (hydroxyacetaldehyde).

The resulting intermediate IV is then reduced (reaction 2, Scheme 1) with aluminium hydrides or with alkaline boronhydrides.

Intermediates II-B can be prepared in different manners, such as for example by subjecting to alkaline hydrolysis the corresponding N-aryl-N-methoxyacetyl-3-amino-1,3-oxazolidin-2-ones described in Belgian Pat. No. 885,117, or according to the reactions reported in the following Scheme 2.

SCHEME 2

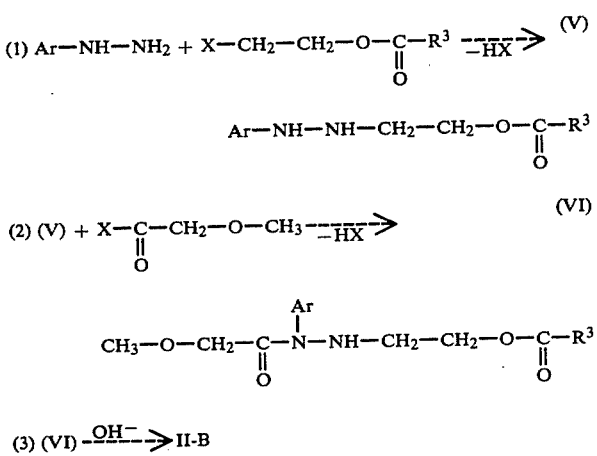

[X = Cl, Br; $R^3$ = lower alkyl]

Reaction 1 consists in condensing an aryl-hydrazine with a haloidrine having the OH group protected in the form of an ester.

Intermediate V so obtained is then acylated (reaction 2) and, finally, the hydroxyl is freed by alkaline hydrolysis (reaction 3).

As mentioned hereinbefore, the compounds of formula I are endowed with a high fungicidal activity.

Their action, which is both of preventive and of curative nature, is directed against various parasitic fungi of plants and seeds, among which we may cite in particular the ones belonging to the family of Phycomycetes, genera Phytophthora, Peronospora and Pythium.

The compounds of formula I possess good systemic properties, wherefore both an application on the leaves and in the soil becomes possible, as well as a sufficient action persistence.

Furthermore, they are consistent with the superior plants without causing any phytotoxicity phenomena in the practical doses of use.

Thanks to their properties it is possible to utilize them for defending a great number of useful plants such as, for example, vine, potato, tobacco, tomato, horticultural plants, fruit-trees, conifers and ornamental plants, from the infections due to fungi.

Thus, it is an object of the present invention to provide a method of controlling infections due to fungi in useful plants, consisting in treating the plants or the soil with an effective amount of a fungicidal compound of formula I.

The effective doses of fungicidal compound to be applied vary as a function of different factors, such as the relative effectiveness of the particular compound employed, the type and degree of the expected or existing infection, the type of culture to be treated, climatic and environmental conditions, etc.

Generally, compound amounts ranging from 10 to 500 g/ha are sufficient for a satisfactory defense of the cultures from the fungi infections.

For practical purposes it is often useful to distribute the compounds of formula I in the form of suitable compositions.

Said compositions contain, besides one or more compounds of formula I as an active substance, a solid or liquid vehicle and optionally other additives.

The compositions may contain from 0.5 to 99% by weight of active substance, depending on the type of composition and on the use it is intended for. According to the usual formulating practice, said compositions may be in the form of granules, dry powders, wettable powders, emulsifiable concentrates etc.

It is particularly useful to employ the compounds of formula I in association with other known fungicides, not only in order to extend and complete the range of action, but also with a view to preventing a possible selection of pathogenous resistant strains and to enhancing, even remarkably, the effectiveness level of each individual compound.

Among the fungicidal compounds subject to be coformulated we may cite:

N-haloalkylthio-imides such as, e.g., the compounds known under the commercial names Captan, Captafol and Folpet;

S-polyhaloalkyl-N-acyl-thiolcarbamates described in Belgian Pat. No. 884,786;

2,4,5,6-tetrachloro-1,3-benzenedicarbonitrile (commercial name Chlorthalonil);

Alkylene-bis-dithiocarbamates of sodium, zinc, manganese and iron;

fungicides based on copper such as, e.g., cupric sulphate, cupric carbonate, copper oxychloride, cupric or cuprous oxide.

In the abovesaid compositions, the weight ratio between the compound of formula I and one of the compounds of the classes listed hereinabove ranges from 1:1 to 1:100.

If desirable, it is possible to add to the fungicidal compositions containing a compound of formula I as active ingredient, also other compatible active substances selected from among insecticides, fertilizers, phyto growth regulators, etc.

The following examples are given to better illustrate the present invention.

EXAMPLE 1

Preparation of compound 1-(2-hydroxyethyl)-2-(2,6-dimethylphenyl)-hydrazine hydrochloride.

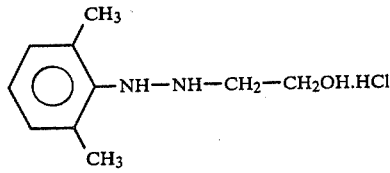

Into a flask equipped with a reflux condenser there were introduced:
6 g of 3-(2,6-dimethylphenylamino)-1,3-oxazolidin-2-one (prepared according to what is described in Belgian Pat. No. 885,117),
1.5 g of ground KOH,
25 ml of ethanol.

The reaction mixture was heated at reflux for 40 minutes and then was poured into water. It was acidified with an aqueous solution of $H_2SO_4$ at 5% and it was washed with ethyl ether (3 times, with 50 ml each time).

The aqueous phase was then made basic with aqueous NaOH and extracted with ethyl ether (2 times, with 50 ml each time).

The ethereal extracts were united and anhydrified on anhydrous $Na_2SO_4$, whereupon the solvent was removed by evaporation under reduced pressure.

3.2 g of the desired product in the form of oil were thus obtained (IR consistent with the assigned structure).

By addition of hydrochloric acid the product crystallized in the form of hydrochloride (melting point=161°–162° C., IR consistent with the assigned structure).

EXAMPLE 2

Preparation of compound 1-(2-hydroxyethyl)-2-methoxy-acetyl-2-(2,6-dimethylphenyl)-hydrazine

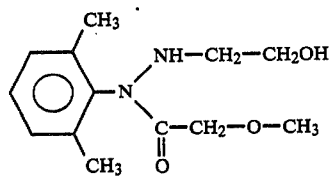

Into a flask equipped with a reflux condenser there were introduced:
5.6 g (0.02 moles) of N-(methoxyacetyl)-N-(2,6-dimethyl-phenyl)-3-amino-1,3-oxazolidin-2-one prepared as described in Belgian Pat. No. 885,117),
1.35 g (0.024 moles) of ground KOH,
25 ml of ethanol The reaction mixture was heated 1 hour at the reflux temperature, then it was poured into water. After acidification, washing with ethyl ether and alkalinization according to the procedures of example 1, the aqueous phase was extracted with ethyl acetate.

The organic phase was anhydrified on anhydrous $Na_2SO_4$ and ethyl acetate was evaporated under reduced pressure.

Thus there were obtained 4.5 g of the desired product in the form of a colorless oil which was crystallized by ethyl ether (white solid, melting point=109°–111° C.).

By treatment with hydrochloric acid, the corresponding hydrochloride was obtained (melting point=141°–142° C.).

EXAMPLE 3

Preparation of compound N-methoxyacetyl-N-(2,6-dimethyl-phenyl)-3-amino-1,3-oxazolidine-2-thione

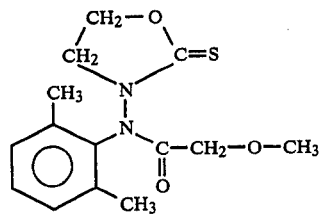

Into a 100-ml flask equipped with a stirrer, a thermometer, a dropping funnel and a reflux condenser connected to a valve with NaOH, there were introduced:
2.5 g (0.01 moles) of 1-(2-hydroxyethyl)-2-methoxyacetyl-2-(2,6-dimethylphenyl)-hydrazine (free base) prepared as described in example 2,
1.6 g (0.02 moles) of pyridine,
50 ml of ethyl acetate.

The mixture was cooled down to 0° C. and, under stirring, it was additioned by dropping thereinto a solution of 1.5 g (0.01 moles) of thiophosgene ($CSCl_2$) in 10 ml of ethyl acetate. About 30 minutes after conclusion of the addition, the temperature was allowed to rise to room temperature, then the reaction mixture was poured into 80 ml of an aqueous solution of $H_2SO_4$ at 5%.

After separation of the organic layer, the aqueous phase was extracted with 30 ml of ethyl acetate.

The united organic phases were anhydrified on anhydrous $Na_2SO_4$.

After removal of the solvent by evaporation under reduced pressure, 2 g of a semisolid product were obtained, which was crystallized by ethyl acetate to yield the desired product (melting point=194°–196° C., IR consistent with the assigned structure).

EXAMPLE 4

Determination of the fungicidal activity against *Peronospora tabacina* (curative activity).

A few tobacco plants cv. Burley cultivated in pot were sprayed, onto the lower face of their leaves, with an aqueous suspension of conides of *P. tabacina* Adam (200,000 conides/ml).

After a 6-hour stay in a moisture-saturated ambient, the plants were divided into two groups and transferred to a conditioned ambient at 20° C. and 70% of relative humidity for the fungus incubation.

48 hours after the infection, a group of plants was treated by spraying both faces of the leaves with a hydroacetonic suspension (20% by volume of acetone) of the product being tested.

At the end of the incubation period (6 days) the infection degree of the treated plants was evaluated in comparison with that of the infected and untreated plants.

At a dose of 100 ppm, the compound of example 3 exhibited an infection reduction of 100%.

EXAMPLE 5

Determination of the fungicidal activity against *Peronospora tabacina* (systemic preventive activity).

A few tobacco plants, cv. Burley, cultivated in pots containing vermiculite, in a conditioned ambient, were sprinkled with a hydroacetonic suspension (20% by vol. of acetone) of the product being tested, after having protected the out-of-soil parts of the plants from a direct contact with the product suspension.

One day after the treatment the lower face of the plants' leaves were sprayed with an aqueous suspension of conides of *P. tabacina Adam* (200,000 conides/ml).

In like manner also a few untreated plants, to be used as check, were infected.

All plants were transferred to a moisture-saturated ambient for 6 hours and then to an ambient conditioned at 20° C. and 70% of relative humidity.

At the conclusion of the fungus incubation period (6 days), the infection degree, due to the fungus, of the treated plants was evaluated in comparison with the infected and untreated plants.

At a dose of 100 ppm referred to the hydroacetonic suspension, the compound of example 3 exhibited an infection reduction of 100%.

EXAMPLE 6

Determination of the fungicidal activity against *Plasmopara viticola* (curative activity).

A few vine plants, cv. Dolcetto, cultivated in pots in a conditioned ambient were sprayed, on the lower face of their leaves, with an aqueous suspension of conides of *P. viticola* (B. and C.) (Berl and de Toni) (200,000 conides/ml).

After a 48-hour stay in a moisture-saturated ambient at 21° C., the plants were divided into two groups.

A group of plants was treated by spraying both faces of the leaves with a hydroacetonic suspension (20% by vol. of acetone) of the product under test.

All plants were then transferred to an ambient conditioned at 25° C. and 60% of relative humidity.

At the conclusion of the fungus incubation period (7 days), the infection degree of the treated plants in comparison with the one of the infected and untreated plants was evaluated.

At a dose of 100 ppm, the compound of example 3 showed an infection reduction of 100%.

EXAMPLE 7

Determination of the fungicidal activity on *Phythium irregulare*.

A culture medium was prepared by hot dissolving 39 g of potato dextrose agar (PDA) and 5 g of yeast extract in 1000 g of water.

Separately, a solution of the product to be tested at a predetermined concentration in dimethylsulphoxide (DMSO) containing 2% of "Tween 20" (wetting agent) was prepared.

At a temperature of 50° C. the DMSO solution was then incorporated into the culture soil at the rate of 1%. The soil so prepared was then introduced into Petri boxes. After cooling, the Petri boxes were inoculated with a disc (diameter=5 mm) of mycelium of the fungus taken from a 4-day-old culture. The fungicidal activity was evaluated by determining the diameter of the colonies after a 72-hour stay at 23° C. in the dark. The compound of example 3 thoroughly prevented the mycelium growth at a dose of 10 ppm.

EXAMPLE 8

Preparation of 2-chloroethyl [2-methoxyacetyl-2-(2-methyl-5-chloro-phenyl)] carbazate.

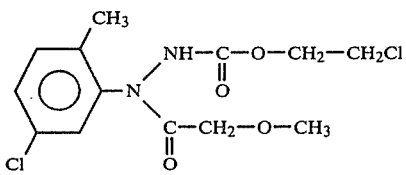

19.3 g (0.1 moles) of 2-methyl-5-chloro-phenylhydrazine hydrochloride were suspended in a mixture of xylene (75 ml) and water (32.5 ml).

To the stirred suspension, 50 ml of an aqueous NaOH solution (8% weight/volume) were added at room temperature.

The resulting mixture was heated up to 35°–40° C. and 14.3 g (0.1 moles) of 2-chloroethyl chloroformiate and 26.6 ml of aqueous NaOH (15% weight/volume) were slowly added to it.

The reaction mixture was stirred for half an hour. The organic layer was then separated and additioned with 12 g (0.11 moles) of methoxyacetyl chloride. The organic mixture was heated up to 50° C. and stirred for half an hour. After cooling a white solid precipitate was formed which was collected by filtration, washed with hexane and dried. 27.8 g of the desired product were obtained as a white solid (m.p.=115°–116° C.).

EXAMPLE 9

Preparation of 1-(2-hydroxy-ethyl)-2-(2-methyl-5-chloro-phenyl)-2-methoxyacetyl-hydrazine

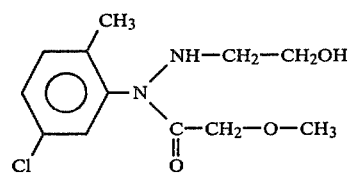

A solution of 6.7 g (0.02 moles) of the carbazate obtained as described in example 8 and of 2.9 g (0.044 moles) of ground KOH in 60 ml of water, was reflux heated for 1 hour.

After cooling at room temperature, the reaction mixture was extracted with methylene-chloride (CH$_2$Cl$_2$) (2×100 ml).

The reunited organic extracts were dried on anhydrous Na$_2$SO$_4$. After evaporation of the solvent at reduced pressure, 5.6 g of a thick oil were obtained. The residue was collected with diethylether (100 ml).

A white solid separated which was collected by filtration, washed with diethylether and dried. 4 g of the desired product were obtained as a white solid (m.p. 92–4° C.).

EXAMPLE 10

Preparation of N-methoxyacetyl-N-(2-methyl-5-chloro-phenyl)-3-amino-1,3-oxazolidin-2-thione

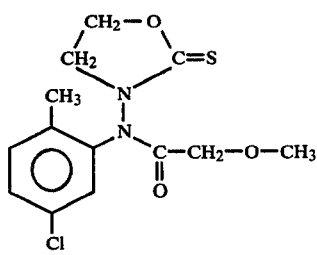

In a 100 ml holding round bottomed flask equipped with stirrer, thermometer, dropping funnel and reflux condenser connected to a NaOH valve, were introduced:

2 g (0.007 moles) of the hydrazine prepared as described in Example 9;
1.12 g (0.014 moles) of pyridine and
20 ml of methylene-chloride ($CH_2Cl_2$).

The stirred mixture was cooled at 0° C. and a solution of 0.8 g (0.007 moles) of thiophosgene ($CSCl_2$) in 5 ml of $CH_2Cl_2$ was dropwise added to it. Half an hour after the addition, the temperature of the reaction mixture was allowed to rise to room temperature.

The reaction mixture was then poured in 50 ml of an aqueous $H_2SO_4$ solution (5% by weight).

The organic phase was separated and dried on anhydrous $Na_2SO_4$.

After removal of the solvent by evaporation at reduced pressure, 2 g of a liquid residue were obtained.

The residue was collected with 10 ml of a 1:1 (v/v) mixture of hexane and ethyl acetate.

A pale yellow solid separated which was collected by filtration, washed with hexane-ethyl acetate (1:1 by volume) and dried. 1 g of the desired product was thus obtained as a solid (m.p. 116–8° C., IR consistent with the assigned structure).

EXAMPLE 11

The compound of Example 10 was tested for fungicidal activity against *Peronospora tabacina* (according to the procedure of Examples 4 and 5) and against *Plasmopara viticola* (according to the procedure of Example 6). In all the tests, the compound of Example 10 showed a complete activity (100% reduction of the fungine infection) at the dose of 100 ppm.

What we claim is:

1. A compound of formula:

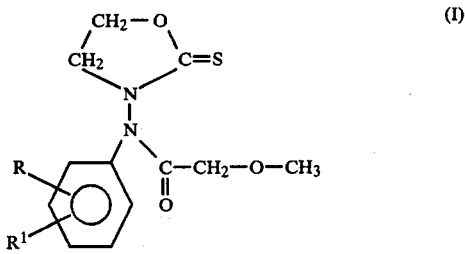

wherein

R and $R^1$, equal to or different from each other, represent an alkyl $C_1$–$C_4$, a halogen atom, an alkoxyl $C_1$–$C_4$.

2. A compound according to claim 1, which is N-methoxyacetyl-N-(2,6-dimethylphenyl)-3-amino-1,3-oxazolidine-2-thione.

3. A compound according to claim 1, which is N-methoxyacetyl-N-(2-methyl-5-chloro-phenyl)-3-amino-1,3-oxazolidine-2-thione.

4. A method of controlling infections due to fungi in useful plants consisting in distributing onto the plants or into the soil an effective amount of one or more of the compounds of claim 1 either as such or in the form of suitable composition.

5. A fungicidal composition containing, as active ingredient, one or more of the compounds of claim 1 besides inert vehicles and optionally other additives.

6. A method of controlling infections due to fungi in useful plants according to claim 4, characterized in that the compound according to claim 1 is the compound of claim 2 or 3.

7. A fungicidal composition according to claim 5, containing as active ingredient the compound of claim 2 or 3.

* * * * *